United States Patent [19]

Kramer et al.

[11] Patent Number: 5,792,113
[45] Date of Patent: Aug. 11, 1998

[54] UNIVERSAL SEAL FOR A TROCAR

[75] Inventors: Francis J. Kramer, Fort Thomas, Ky.; Hector Chow, Cincinnati, Ohio

[73] Assignee: Ethicon Endo-Surgerym Inc., Cincinnati, Ohio

[21] Appl. No.: 766,393

[22] Filed: Dec. 12, 1996

[51] Int. Cl.$^6$ .................................................. A61M 29/02
[52] U.S. Cl. .................................... 604/167; 604/256
[58] Field of Search ................................. 604/164, 166, 604/167, 264, 185

[56] References Cited

U.S. PATENT DOCUMENTS

| | | | |
|---|---|---|---|
| 4,240,411 | 12/1980 | Hosono | 604/167 |
| 5,167,636 | 12/1992 | Clement | 604/167 |
| 5,197,955 | 3/1993 | Stephens et al. | 604/167 |
| 5,209,736 | 5/1993 | Stephens et al. | 604/164 |
| 5,242,412 | 9/1993 | Blake, III | 604/167 |
| 5,308,336 | 5/1994 | Hart et al. | 604/167 |
| 5,338,307 | 8/1994 | Stephens et al. | 604/167 |
| 5,342,315 | 8/1994 | Rowe et al. | 604/167 |
| 5,385,553 | 1/1995 | Hart et al. | 604/167 |
| 5,395,342 | 3/1995 | Yoon | 604/167 |
| 5,407,433 | 4/1995 | Loomas | 604/167 |
| 5,411,483 | 5/1995 | Loomas et al. | 604/167 |
| 5,492,304 | 2/1996 | Smith et al. | 251/149.1 |
| 5,545,142 | 8/1996 | Stephens et al. | 604/167 |
| 5,603,702 | 2/1997 | Smith et al. | 604/167 X |

*Primary Examiner*—Michael A. Brown
*Attorney, Agent, or Firm*—Matthew S. Goodwin

[57] ABSTRACT

A universal seal for a trocar is disclosed. The universal seal has a rigid housing with a chamber for receiving a sealing assembly. The sealing assembly is disposed within the chamber and has freedom of movement along the longitudinal axis of the housing in response to a surgical instrument being inserted into or withdrawn from the sealing assembly. The sealing assembly includes first and second rigid rings generally parallel to and spaced from each other. It also includes an inner elastomeric seal for sealing against instruments of varying diameter. The inner elastomeric seal is attached to the second ring, and it has an aperture for passage of an instrument through the elastomeric seal. In response to off-centered insertion of an instrument into the universal seal, the sealing assembly moves longitudinally and assumes a tilted orientation as the radial force on the inner elastomeric seal is applied by the instrument. The aperture of the inner elastomeric seal consequently moves laterally in response to the off-centered insertion, thus preventing the aperture from stretching significantly or tearing. Therefore, the sealing assembly of the universal seal reduces the escape of insufflation gases from the surgical site through the seal when instruments over a very wide range of diameters are inserted into or withdrawn from the seal.

8 Claims, 8 Drawing Sheets

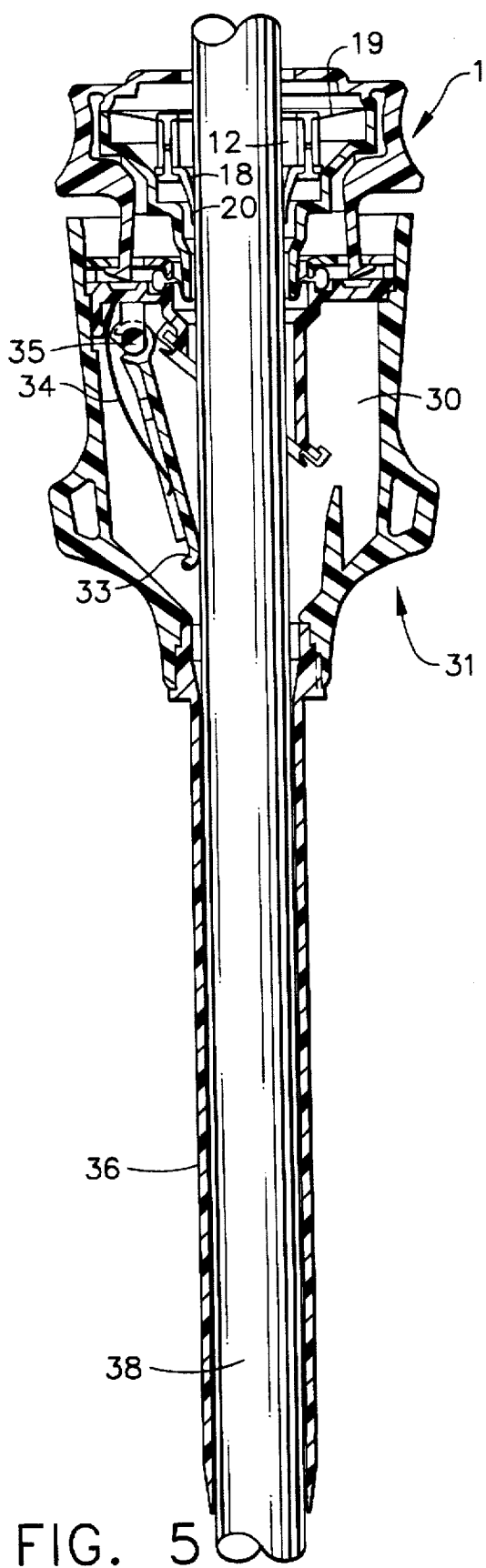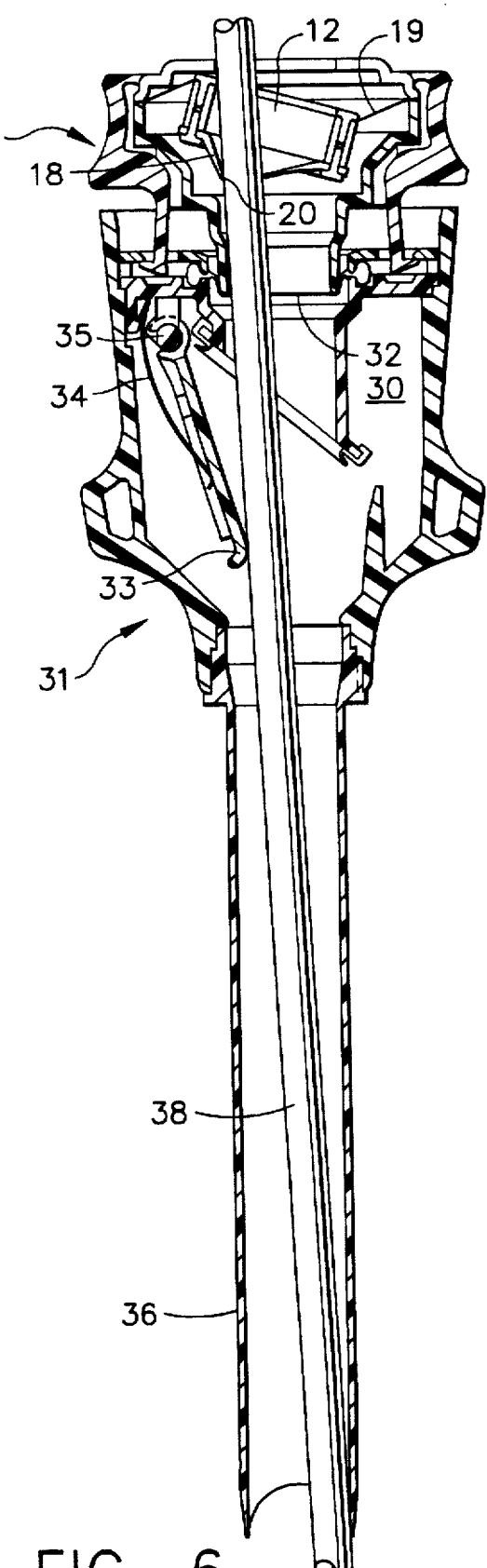

UNIVERSAL SEAL FOR A TROCAR

BACKGROUND OF THE INVENTION

This invention relates generally to a surgical trocar for puncturing the body wall of a patient to provide access to a surgical site during endoscopic surgery. More specifically, it relates to a universal seal for a trocar to minimize or prevent leakage of insufflation fluid from the surgical site through the trocar when instruments are inserted into or withdrawn from the trocar.

A critical feature of a trocar is the design of the seal which prevents the passage of insufflation fluid through the trocar when instruments of varying sizes are inserted into or withdrawn from it. During endoscopic surgery, the abdomen is "insufflated" with carbon dioxide gas under pressure to provide space between internal organs and bodily tissue during surgical procedures. First, the trocar obturator, which is the puncturing implement of the trocar assembly, is used to puncture the abdominal wall. The trocar obturator is subsequently removed, the abdomen is inflated, and the trocar cannula remains in place to provide access for surgical instruments to the surgical site. The cannula has a housing and a cannula tube extending from the housing. It is the housing which contains the seal. The housing also contains a valve, typically a flapper valve. When an instrument is inserted through the cannula, the instrument is inserted through the seal and causes the flapper valve to swing out of the way. The seal conforms to the outer diameter of the instrument, and therefore prevents the insufflation gas from exiting the body through the housing of the cannula. When the instrument is removed, the flapper valve automatically swings shut to likewise prevent insufflation gas from escaping.

One type of seal for a trocar is a simple gasket fixed to the cannula housing which has a diameter sized for the insertion and withdrawal of instruments of generally fixed diameter. Although simple in construction, it has the disadvantage of not being able to seal against instruments which have a diameter smaller that that for which the seal was sized. Accordingly, a reducer cap with a gasket diameter smaller than that of the housing to accommodate smaller sized instruments has been developed. The cap snaps onto the housing. Therefore, the surgeon can choose between the larger, fixed gasket of the housing or the smaller one on the reducer cap to ensure that an adequate seal around the instrument would be maintained when the instrument is inserted through the cannula. This reducer cap is described in U.S. Pat. No. 5,338,307.

While the reducer cap provides a greater degree of flexibility for inserting instruments with varying diameters through the cannula, it still requires the surgeon to manipulate the cap to provide the proper seal. Accordingly, efforts have been undertaken to develop an improved seal for a trocar.

A description of the first "universal seal" for a trocar is set forth in U.S. Pat. No. 5,395,342. The seal described in the '342 patent has an elastomeric cone with an aperture at its apex. The cone is fitted over a plurality of resilient legs extending from a frame fixed to the cannula housing. When an instrument is inserted through the seal, the instrument contacts the legs and causes them to expand against the elastomeric cone. This expansion facilitates the expansion of the aperture so it will conform to the outer diameter of the instrument.

Significantly, the '342 patent provides the first description which inherently recognizes the less than desirable overall performance of seals composed of conventional elastomeric materials, such as silicone. Accordingly, it describes the use of resilient legs to facilitate the expansion of the seal, which is a key factor in the overall performance of the seal. Consequently, the likelihood that the aperture of the elastomeric seal will tear and thus allow significant leakage of insufflation gas through the cannula is dramatically reduced.

In addition to the use of resilient legs to facilitate expansion of the aperture in the seal, seal designs have been developed to protect or shield the elastomeric seal from puncture during instrument insertion. For example, U.S. Pat. No. 5,342,315 describes the use of "protectors" surrounding the elastomeric seal which come into direct contact with the instrument during instrument insertion. The protectors prevent direct contact of the instrument tip with the elastomeric seal, and therefore significantly minimize or prevent the instrument tip from puncturing the outer periphery of the seal. Another protector configuration designed to isolate the instrument from the outer periphery of the elastomeric seal is described in U.S. Pat. No. 5,308,336.

Furthermore, the ability to "offset" the aperture of the seal by enabling lateral movement of the seal in response to off-centered insertion of an instrument through the seal has been recognized to reduce the amount of stretching or tearing of the aperture. Leakage of insufflation fluid is therefore minimized. See, for example, U.S. Pat. Nos. 5,209,736; 5,407,433 and 5,411,483.

Although universal seals for trocars have been developed to prevent the escape of insufflation gases from the surgical site when instruments of varying diameter are inserted or withdrawn for the trocar, improvements and variations of these seals are still being sought. Specifically, it would be highly desirable to develop a universal seal for a trocar which provides for the ability to offset the aperture of the seal in response to off-centered insertion of an instrument. In this way, the aperture could be prevented from stretching or tearing, thus preventing leakage of insufflation fluid through the seal.

SUMMARY OF THE INVENTION

The invention is a universal seal for a trocar. The universal seal comprises a rigid housing and a sealing assembly. Each of these two elements of the universal seal will now be briefly described.

The rigid housing of the universal seal is adapted to be mounted onto a cannula of the trocar. The housing has a longitudinal axis and a chamber inside the housing for receiving a sealing assembly. The housing has a top face and a bottom face. The top and bottom faces both have an opening in them for providing a pathway through the housing into the cannula.

The sealing assembly of the universal seal is disposed within the chamber of the rigid housing for movement along the longitudinal axis of the housing in response to a surgical instrument being inserted into or withdrawn from the sealing assembly. The sealing assembly includes first and second rigid rings generally parallel to and spaced from each other. The sealing assembly also includes an inner elastomeric seal located in the pathway through the housing for sealing against the surgical instrument over a range of instrument diameters. The elastomeric seal is attached to the second ring and spaced from the first ring. Further, the elastomeric seal has an aperture in it for passage of the instrument through the elastomeric seal.

The universal seal of this invention can be mounted on a trocar to seal against surgical instruments over a wide range of diameters to maintain insufflation in the body cavity during endoscopic surgery. As of the filing date of the application which matured into this patent, surgical instruments with diameters between 5–12 mm have conventionally been used during endoscopic surgery. Consequently, the universal seal of this invention for a trocar can accommodate the insertion and withdrawal of instruments with diameters in this range. In addition, the universal seal of this invention can accommodate instruments within a wider or narrower range of diameters.

Significantly, the freedom of the sealing assembly of the universal seal of this invention to move along the longitudinal axis of the housing in response to insertion or withdrawal of surgical instruments reduces the tendency of the inner elastomeric seal to tear or significantly stretch, thus minimizing leakage of insufflation gasses from the surgical site through the universal seal. Specifically, when the instrument comes into contact with the inner elastomeric seal of the sealing assembly, particularly when it contacts the elastomeric seal off-centered from the longitudinal axis of the housing, the instrument applies a radial force on the inner seal of the sealing assembly. Since the sealing assembly has freedom of longitudinal movement, the sealing assembly will correspondingly move longitudinally in response to instrument insertion. Importantly, however, concurrently with this longitudinal movement, the sealing assembly will "tilt" its orientation, and consequently the aperture of the elastomeric seal will reposition itself in response to the off-center direction in which the instrument is inserted or withdrawn. Accordingly, the aperture of the elastomeric seal moves laterally in response to the movement of the instrument, and therefore the aperture is not subjected to significant stretching. In this manner, leakage of insufflation gases from the surgical site through the aperture, particularly when an instrument is inserted through the aperture in an off-centered direction relative to the longitudinal axis of the housing, is prevented. Additionally, the tearing tendency for of the inner elastomeric seal is significantly reduced.

In a preferred embodiment of the invention, a rigid ring connector connects the first and second rings to each other, and the first rigid ring of the sealing assembly is attached to an outer seal spaced from the inner elastomeric seal and located peripherally of the pathway through the housing for minimizing the escape of insufflation gases from a surgical site through the chamber of the housing. In this particular embodiment, the outer seal is secured to the housing and it is composed of a material which is compliant along the longitudinal axis of the housing. Accordingly, the escape of insufflation gases from the body cavity through the sealing assembly is further minimized, and depending upon the material of which the outer seal is composed, the range of movement along the longitudinal axis of the housing and the degree of resistance to such movement, can be controlled.

The universal seal of this invention can be used on all of the trocars which have conventionally been used or contemplated for use in surgical procedures. Of course, the universal seal of this invention is particularly adapted for endoscopic applications where it is necessary to insert instruments of varying diameter through a trocar while still maintaining insufflation within the body cavity.

BRIEF DESCRIPTION OF THE DRAWINGS

FIGS. 5 and 6 represent plan view sections illustrating the insertion of instruments of varying diameters through the universal seal depicted in FIGS. 3 and 4 mounted onto a trocar cannula.

DETAILED DESCRIPTION OF THE PREFERRED EMBODIMENTS

Figure 3:
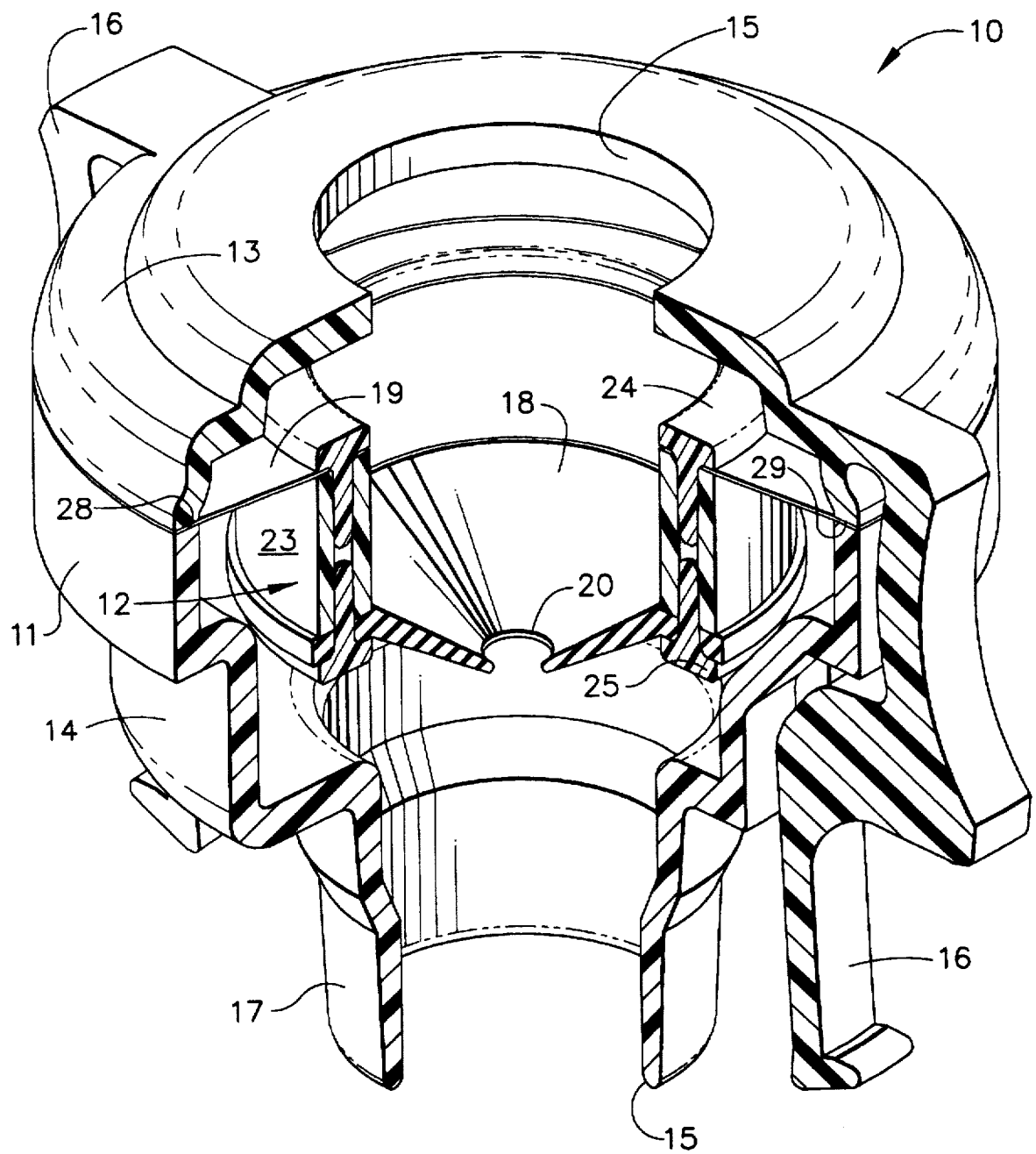
FIG. 3 is a perspective view partially broken away showing the structure of the first embodiment of the universal seal of this invention.
Figure 4:
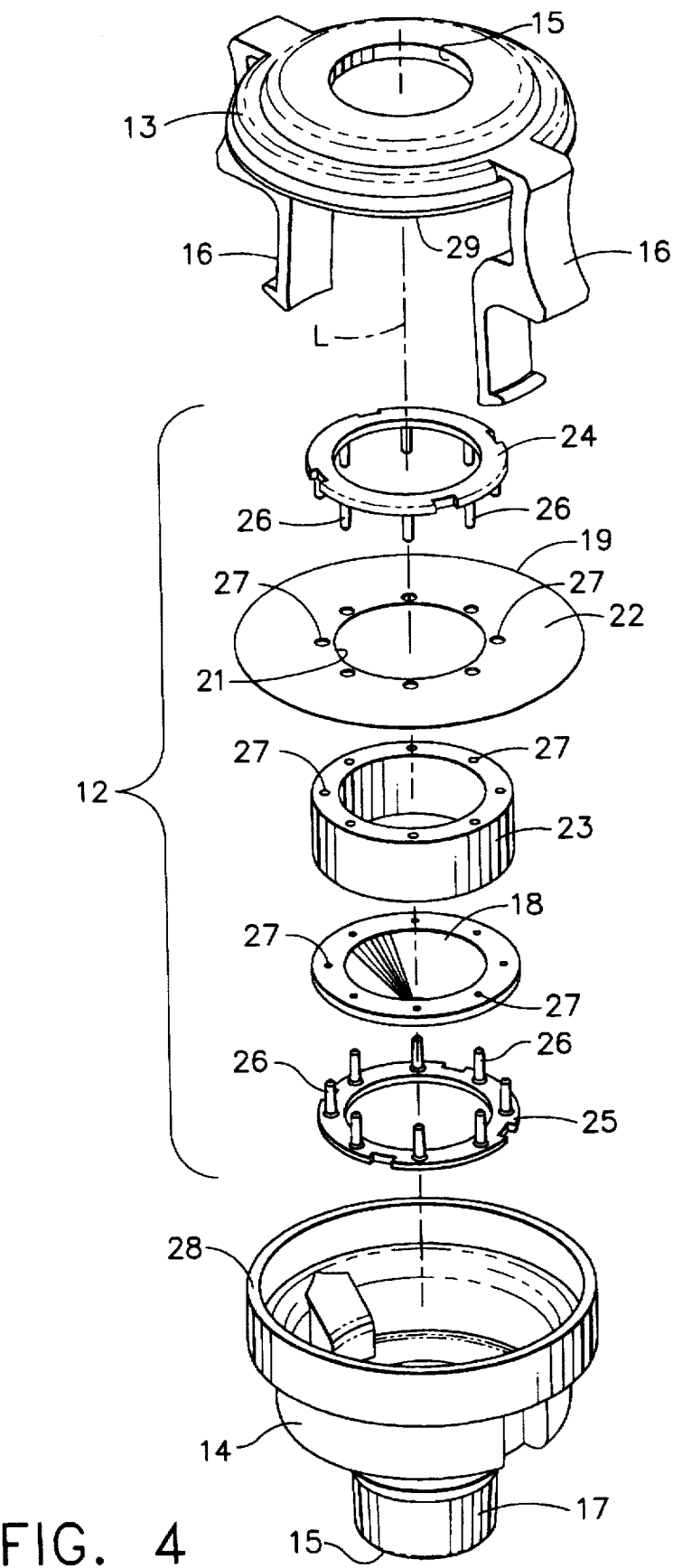
FIG. 4 is an exploded perspective view of the universal seal depicted in FIG. 3.
Figure 7:
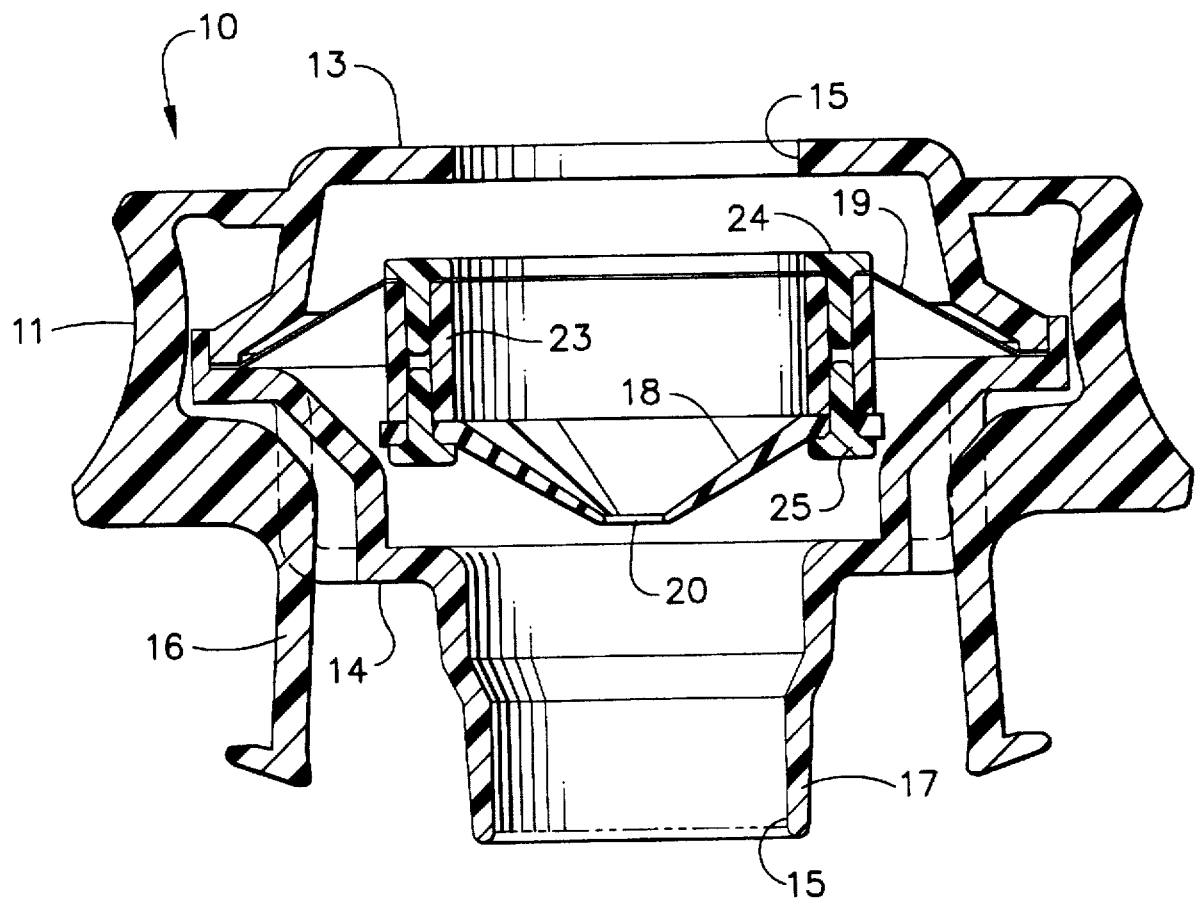
FIG. 7 is a plan view section taken through the centerline axis of a second embodiment of a universal seal of this invention.
Figure 8:
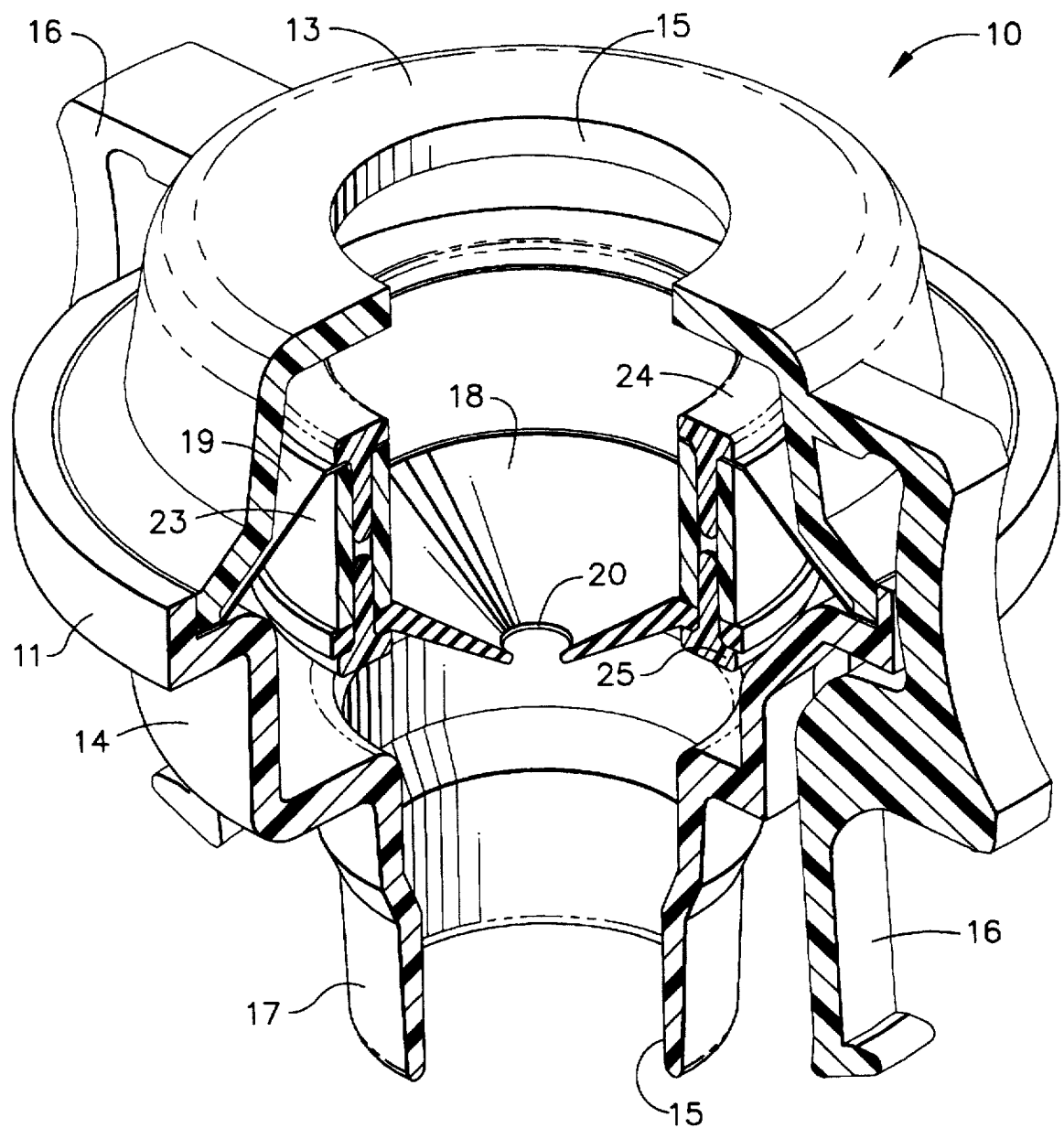
FIG. 8 is a perspective view partially broken away showing the structure of the universal seal depicted in FIG. 7.
Figure 9:
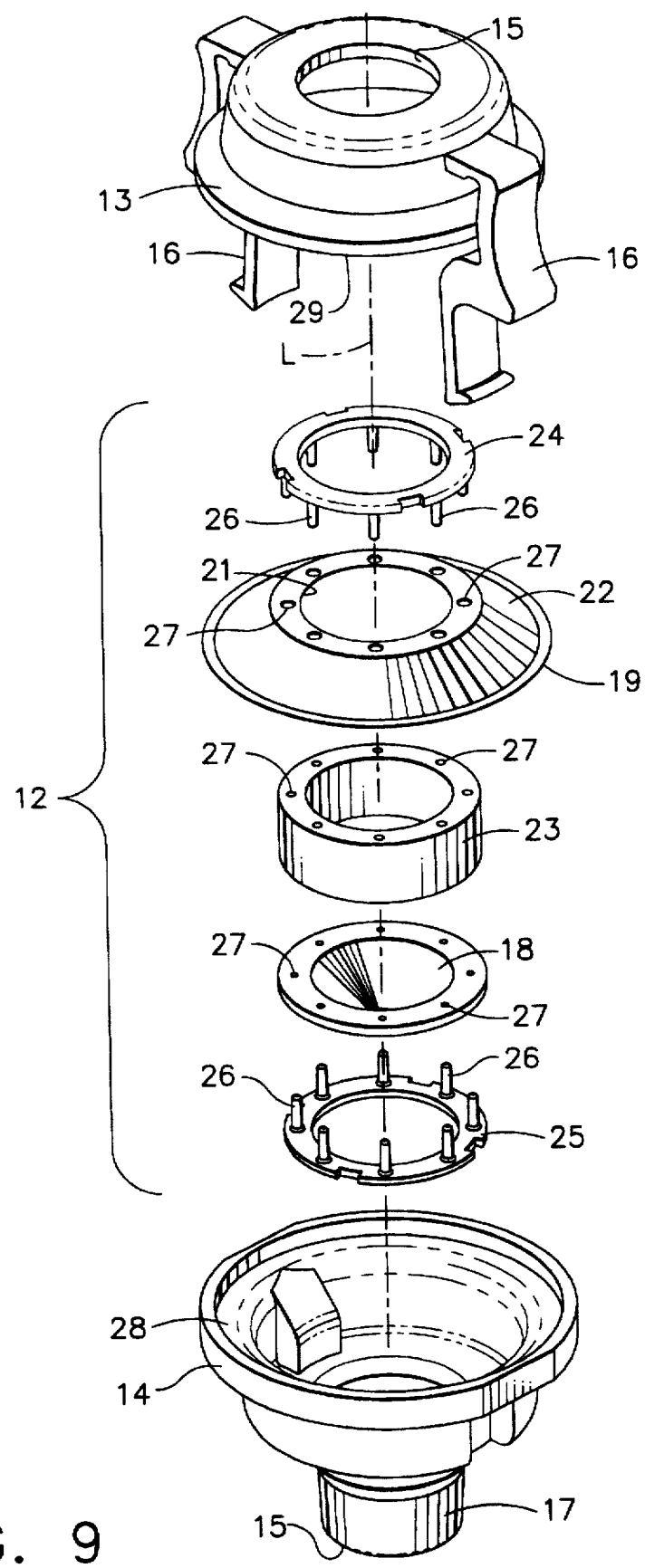
FIG. 9 is an exploded perspective view of the universal seal depicted in FIGS. 7 and 8.

Referring initially to FIGS. 3 and 4 illustrating the first preferred embodiment of the universal seal of this invention, the reader will note that the universal seal 10 is a multi-component assembly. The seal, when assembled, has a rigid housing 11 with a sealing assembly 12 disposed inside the housing. The housing has top and bottom faces 13 and 14, respectively. Each of the faces has an opening 15 through it to create a pathway through the universal seal. The top face includes a pair of spring-biased latches 16 for coupling the universal seal to the trocar cannula. The bottom face of the rigid housing has a tubular neck 17 to facilitate the guidance of instruments inserted through the seal into the trocar cannula.

The sealing assembly includes an inner conical seal 18 and an outer seal 19. The inner conical seal is situated in the pathway existing through the universal seal between the openings in the top and bottom faces of the rigid housing. The inner seal has a seal aperture 20 which is sized to substantially conform to the smallest diameter instrument which is contemplated to be inserted through the trocar cannula. The inner seal is designed to seal against instruments of varying diameter, particularly instruments having diameters ranging from about 3–12 mm. The inner conical seal is preferably composed of a silicone elastomer which exhibits an elongation of at least about four hundred percent (400%) and a modulus not greater than about 500 psi, as determined in accordance with ASTM Test Method D882.

The outer seal 19 is a seal shaped in the form of a doughnut. The doughnut hole 21 of the outer seal corresponds in size to the size of the pathway located through the top and bottom faces of the rigid housing of the universal seal to enable the unrestricted passage of the largest diameter instruments through it. The sealing portion 22 of the doughnut-shaped outer seal is composed of a material which is sufficiently compliant to provide for longitudinal movement of the outer seal despite the fact that it is secured along its circumferential edge to the rigid housing. In addition to enabling the longitudinal movement of the sealing assembly of the universal seal, the outer seal also prevents insufflation gases from escaping the space created by the difference in diameter of the inner conical seal and the rigid housing. The outer seal is preferably composed of an elastomer which exhibits a modulus of at least about 800 psi, determined in accordance with ASTM Test Method D882.

The inner and outer seals, 18 and 19, are spaced from each other along the longitudinal axis denoted as "L" (in FIG. 4)

by a rigid ring connector 23. First and second rigid rings, 24 and 25, respectively, fasten the outer and inner seals to the rigid ring connector. The first and second rigid rings each have a plurality of prongs 26 which are received in a plurality of holes 27 located in the inner and outer seals, as well as the rigid ring connector. Once the components of the sealing assembly are coupled to each other, the sealing assembly is situated inside the bottom face 14 of the rigid housing. The circumferential edge of the outer seal 19 is seated on a seating surface 28 at the upper edge of the housing bottom face. The top face 13 is then fixedly attached by ordinary means the bottom face so that a mating surface 29 on the housing top face sandwiches the circumferential edge of the outer seal between the mating surface 29 and the seating surface 28 of the housing bottom face.

Figure 1:
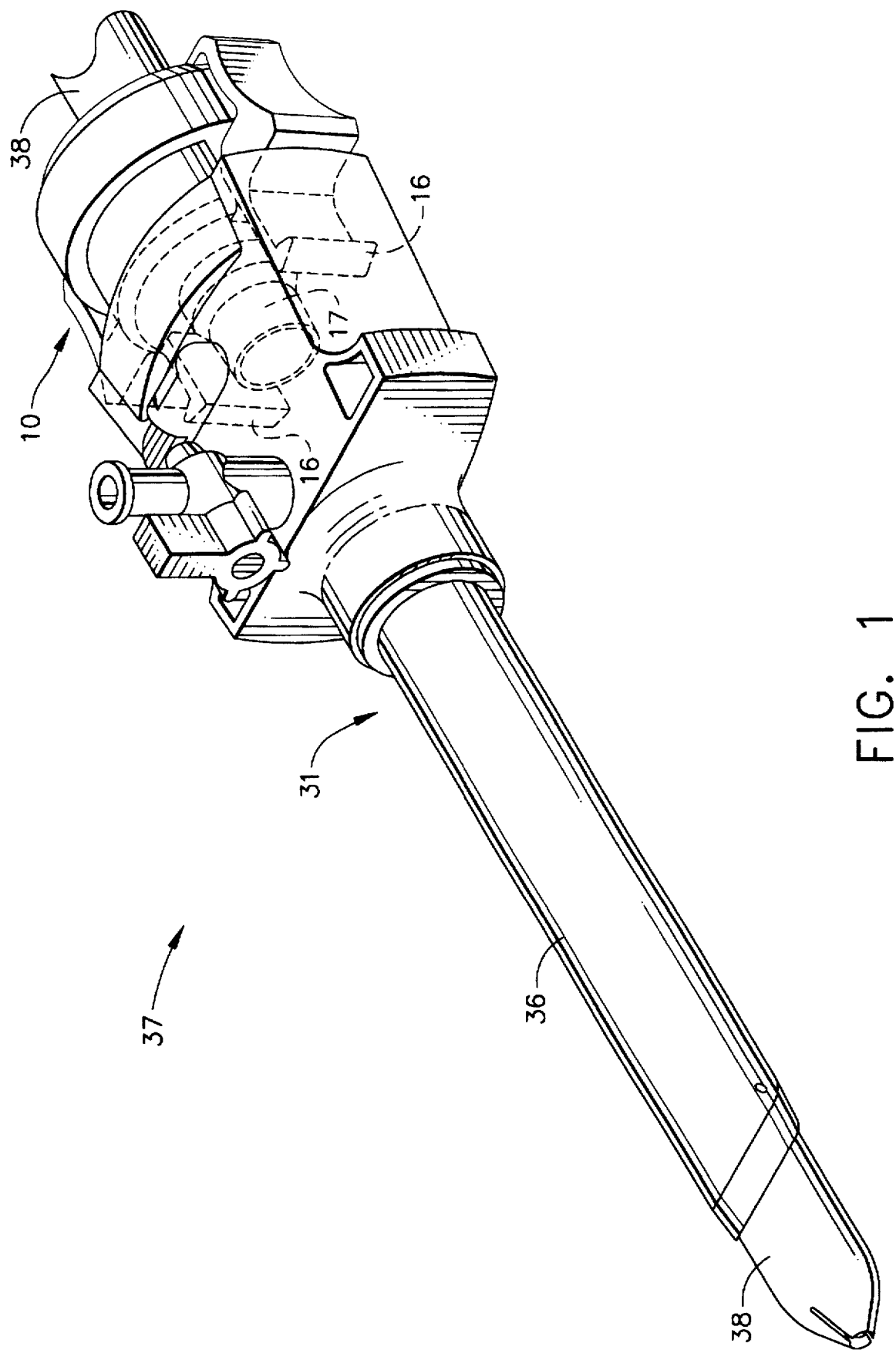
FIG. 1 is a perspective view of a first embodiment of a universal seal of this invention mounted onto a trocar cannula.
Figure 2:
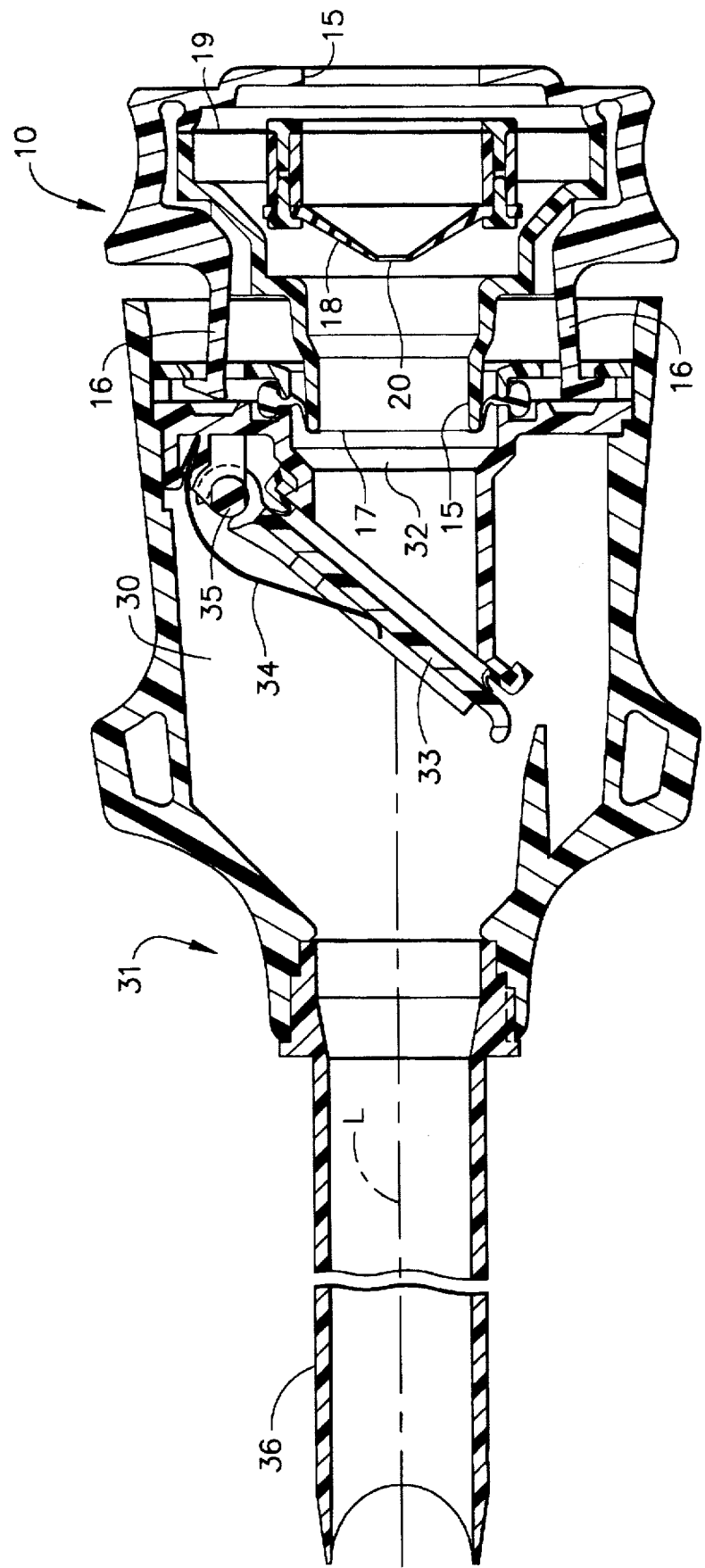
FIG. 2 is a plan view section taken through the centerline axis of the cannula depicted in FIG. 1.

Referring to FIGS. 1 and 2, the universal seal 10 is mounted to the housing of the trocar cannula when the latches 16 on the housing top surface are forced inwardly, and received within the vestibule 30 of the trocar cannula 31. Once inward pressure on the latches is removed, the spring force of the latches applied against the inner walls of the vestibule secures the universal seal to the cannula housing.

The universal seal can be adapted to mount onto a conventional trocar cannula. When mounted, the tubular neck 17 descending from the housing bottom face of the universal seal is advantageously seated adjacent the orifice 32 of the cannula housing. The cannula housing includes a flapper valve 33 which is biased in the closed position by the spring force of the flapper spring 34, and is capable of pivoting about a valve pivot 35. The flapper valve prevents escape of insufflation gas during minimally invasive surgery when an instrument has not been inserted through the trocar cannula. Of course, a cannula tube 36 extends from the housing and provides access to the surgical site within the body cavity once an opening is made with, for example, a safety shielded trocar 37 as depicted in FIG. 1.

Turning now to FIG. 2 in combination with FIGS. 5 and 6, there is shown the universal seal mounted on the housing of the trocar cannula when an instrument has not been inserted through it (FIG. 2) , and when instruments 38 of varying diameter have been inserted through it (FIGS. 5 and 6). Noting FIG. 2 first, it will be observed that the rest postion of the sealing assembly within the rigid housing of the universal seal is such that the outer seal 19 is generally perpendicular to the longitudinal axis, L, of the trocar cannula 31. When an instrument 38 having a diameter corresponding in size to the diameter of the inner diameter of the cannula tube is inserted through the universal seal, FIG. 5 depicts the configuration of the sealing assembly providing a seal against this instrument. In this particular instance, the diameter of the pathway through the universal seal is sized to generally match the diameter of the instrument depicted in FIG. 5. When the instrument is inserted, the reader will note that the sealing assembly moves downwardly within the rigid housing of the universal seal in response to the downward movement of the outer seal. The aperture 20 of the inner seal 18 within the sealing assembly of the universal seal stretches to fit around the instrument, thus providing the requisite seal for the instrument having the diameter depicted in FIG. 5.

Turning now to FIG. 6, an instrument 38 having a diameter smaller than those of either the pathway through the universal seal or the cannula tube 36 is inserted through the trocar cannula. Consequently, it is likely that the instrument will not be inserted perfectly parallel with the longitudinal axis of the trocar cannula, therefore leading to what is referred to as "offset" insertion. In response to this offset insertion, uneven lateral and longitudinal forces are applied against the sealing assembly 12 of the universal seal. In a conventional sealing gasket assembly, these uneven forces would cause the inner sealing gasket to undesirably stretch significantly. This stretching would lead to the creation of openings through the seal despite engagement of the seal with the instrument or worse yet, tearing of the sealing gasket. In contrast, the sealing assembly in the universal seal of this invention can accommodate these uneven forces because the compliant nature of the outer seal 19 enables longitudinal movement of the sealing assembly. During offset insertion as depicted in FIG. 6, a portion of the sealing assembly will move proximally and the opposite portion will move distally, which will cause a radial "tilting" to accommodate the sealing about the smaller diameter instrument. Unlike a conventional seal, the radial reorientation of the sealing assembly lessens or eliminates the stresses imposed on the aperture of the inner seal which is designed to seal about instruments of varying diameter. Thus, a successful seal can be maintained, and tearing of the seal aperture can be prevented.

A second embodiment of the universal seal of this invention is illustrated in FIGS. 7–10. Reference numerals which have been designated for the component parts of the universal seal 10 of the first embodiment illustrated in FIGS. 1–6 are the same reference numerals designated to denote the identical component parts of the second embodiment for ease of review and reference. The relationships between the component parts is substantially identical for the two embodiments, as well as the principles of operation. The primary difference structurally between the second and first embodiments is that in the second embodiment depicted in FIGS. 7–9, the outer doughnut-shaped seal 19 has a conical configuration, and the top housing face 13 of the rigid housing 11 is shaped to accommodate the conical shape of the outer seal.

Although this invention has been described in connection with its preferred embodiments, these embodiments are illustrative only and the scope of the claimed invention is to be determined in connection with the claims which appear below.

What is claimed is:

1. A universal seal for a trocar comprising:
   a) a rigid housing adapted to be mounted onto a cannula of said trocar, said housing having a longitudinal axis and a chamber therein for receiving a sealing assembly, and said housing having a top face and a bottom face, wherein each of said faces has an opening therein for providing a pathway through said housing into said cannula; and
   b) a sealing assembly disposed within said chamber of said rigid housing, said sealing assembly movable along the longitudinal axis of said housing in response to a surgical instrument being inserted into or withdrawn from said sealing assembly; said sealing assembly including:
      i) first and second rigid rings generally parallel to and spaced longitudinally from each other;
      ii) an inner elastomeric seal located in the pathway through said housing for sealing against said surgical instrument of varying diameter, said elastomeric seal attached to said second ring and spaced longitudinally from said first ring, and said elastomeric seal having an aperture therein for passage of said instrument through said elastomeric seal; and
      iii) an outer seal attached to said first rigid ring and spaced longitudinally from said inner elastomeric seal and located peripherally of the pathway of said housing for minimizing the escape of insufflation gases from a surgical site through said chamber of said housing.

2. The universal seal of claim 1 wherein said sealing assembly includes a rigid ring connector located inside said rigid housing and connecting said first and second rings to each other.

3. The universal seal of claim 2 wherein said outer seal is secured to said housing and is composed of a material which is compliant along the longitudinal axis of said housing.

4. The universal seal of claim 3 wherein said inner elastomeric seal is a conical seal.

5. The universal seal of claim 4 wherein said outer seal is generally planar.

6. The universal seal of claim 5 wherein said inner elastomeric seal is composed of a silicone elastomer exhibiting an elongation of at least about 400% and a modulus no greater than about 500 psi.

7. The universal seal of claim 6 wherein said outer seal is composed of an elastomer exhibiting a modulus of at least about 800 psi.

8. The universal seal of claim 7 wherein said bottom face of said rigid housing has a tubular neck descending therefrom for guiding said instrument through said housing into said cannula.

* * * * *